United States Patent [19]

Schenker

[11] 4,263,298
[45] Apr. 21, 1981

[54] HYDRAZINO BICYCLIC PYRIDAZINES AS HYPERTENSIVES

[75] Inventor: Erhard Schenker, Basel, Switzerland

[73] Assignee: Sandoz Ltd., Basel, Switzerland

[21] Appl. No.: 54,631

[22] Filed: Jul. 3, 1979

Related U.S. Application Data

[60] Division of Ser. No. 854,332, Nov. 23, 1977, Pat. No. 4,181,273, which is a continuation of Ser. No. 748,743, Dec. 9, 1976, abandoned, which is a continuation of Ser. No. 492,064, Jul. 26, 1974, abandoned.

[30] Foreign Application Priority Data

Aug. 2, 1973 [CH]  Switzerland ............... 11217/73
Dec. 21, 1973 [CH]  Switzerland ............... 18036/73

[51] Int. Cl.³ ............... A61K 31/50; C07D 237/28; C07D 237/26; C07D 471/04
[52] U.S. Cl. ............... 424/250; 544/235; 544/236; 260/326.4; 260/326.8; 546/281; 546/242; 542/427
[58] Field of Search ............... 544/36; 424/250; 542/427

[56] References Cited

U.S. PATENT DOCUMENTS 3,838,125   9/1974   Shenker ............... 544/236

OTHER PUBLICATIONS

Shenker I, Chem. Abs. 78, 43502t (1972).
Shenker III, Chem. Abs. 83, 28261-3 (1975).
Shenker II, Chem. Abs. 83, 11450-6 (1975).
Shenker V, Chem. Abs. 83, 206311 (1975).

*Primary Examiner*—Mark L. Berch
*Attorney, Agent, or Firm*—Gerald D. Sharkin; Robert S. Honor; Thomas O. McGovern

[57] ABSTRACT

This invention provides new compounds of formula I,

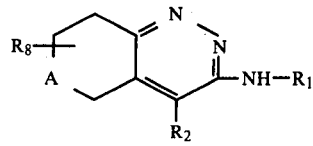

wherein
$R_1$ is amino, or

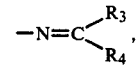

wherein each of $R_3$ and $R_4$ is independently alkyl of 1 to 4 carbon atoms,
$R_2$ is alkyl of 1 to 4 carbon atoms or phenyl,
$R_8$ is hydrogen or alkyl of 1 to 4 carbon atoms, and
A is $-(CH_2)_n-$,
wherein n is an integer from 1 to 3, with the proviso that when $R_1$ is amino, $R_2$ is methyl or phenyl and $R_8$ is hydrogen,
n is 2 or 3,
or $=N-CO-R_5$,
wherein $R_5$ is alkyl of 1 to 6 carbon atoms, alkenyl of 3 to 6 carbon atoms, a $-(CH_2)_m-R_6$ group, wherein
m is an integer from 0 to 2, and
$R_6$ is phenyl, or phenyl monosubstituted by fluorine, chlorine, bromine, alkyl of 1 to 4 carbon atoms, alkoxy of 1 to 4 carbon atoms or alkylmercapto of 1 to 4 carbon atoms,
or an $-OR_7$ group,
wherein $R_7$ is alkyl of 1 to 4 carbon atoms, alkenyl of 2 to 4 carbon atoms, phenylalkyl of 7 to 10 carbon atoms, phenylalkyl of 7 to 10 carbon atoms monosubstituted in the phenyl ring by chlorine, alkoxy of 1 to 4 carbon atoms or alkyl of 1 to 4 carbon atoms; phenylalkenyl of 8 to 10 carbon atoms, or phenylalkenyl of 8 to 10 carbon atoms monosubstituted in the phenyl ring by chlorine, alkoxy of 1 to 4 carbon atoms or alkyl of 1 to 4 carbon atoms, useful as anti-hypertensives.

6 Claims, No Drawings

HYDRAZINO BICYCLIC PYRIDAZINES AS HYPERTENSIVES

This is a division of application Ser. No. 854,332, filed Nov. 23, 1977, now U.S. Pat. No. 4,181,273 which in turn is a continuation, application Ser. No. 748,743, filed Dec. 9, 1976, now abandoned, which in turn is a continuation of Ser. No. 492,064, filed July 26, 1974, now abandoned.

The present invention relates to new heterocyclic compounds.

In accordance with the invention there are provided new compounds of formula I,

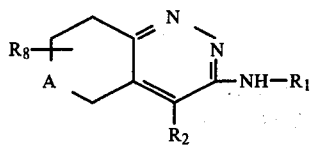

wherein
$R_1$ is amino, or

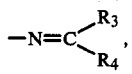

wherein each of $R_3$ and $R_4$ is independently alkyl of 1 to 4 carbon atoms,
$R_2$ is alkyl of 1 to 4 carbon atoms or phenyl,
$R_8$ is hydrogen or alkyl of 1 to 4 carbon atoms, and
A is $-(CH_2)_n-$,
wherein n is an integer from 1 to 3, with the proviso that when $R_1$ is amino, $R_2$ is methyl or phenyl and $R_8$ is hydrogen,
n is 2 or 3,
or $=N-CO-R_5$,
wherein $R_5$ is alkyl of 1 to 6 carbon atoms, alkenyl of 3 to 6 carbon atoms, a $-(CH_2)_m-R_6$ group, wherein m is an integer from 0 to 2, and
$R_6$ is phenyl, or phenyl monosubstituted by fluorine, chlorine, bromine, alkyl of 1 to 4 carbon atoms, alkoxy of 1 to 4 carbon atoms or alkylmercapto of 1 to 4 carbon atoms,
or an $-OR_7$ group,
wherein $R_7$ is alkyl of 1 to 4 carbon atoms, alkenyl of 2 to 4 carbon atoms, phenylalkyl of 7 to 10 carbon atoms, phenylalkyl of 7 to 10 carbon atoms monosubstituted in the phenyl ring by chlorine, alkoxy of 1 to 4 carbon atoms or alkyl of 1 to 4 carbon atoms; phenylalkenyl of 8 to 10 carbon atoms, or phenylalkenyl of 8 to 10 carbon atoms monosubstituted in the phenyl ring by chlorine, alkoxy of 1 to 4 carbon atoms or alkyl of 1 to 4 carbon atoms.

Further, in accordance with the invention a compound of formula I may be obtained by a process comprising (a) producing a compound of formula Ia,

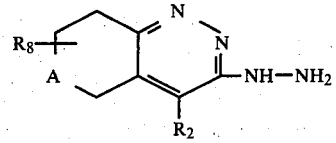

wherein $R_2$, $R_8$ and A are as defined above, by reacting a compound of formula II,

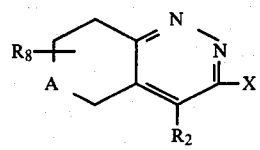

wherein
$R_2$, $R_8$ and A are as defined above, and
X is chlorine, bromine, mercapto or $-SR_9$,
wherein $R_9$ is benzyl or alkyl of 1 to 4 carbon atoms,
with hydrazine, or (b) producing a compound of formula Ib,

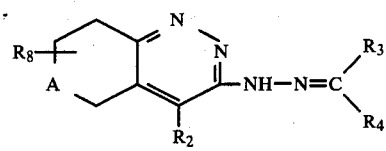

wherein $R_2$, $R_3$, $R_4$, $R_8$ and A are as defined above, by reacting a compound of formula Ia with a compound of formula III,

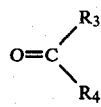

wherein $R_3$ and $R_4$ are as defined above.
When $R_1$ is an

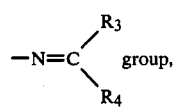

group, the alkyl radicals $R_3$ and $R_4$ therein especially signify methyl or ethyl groups.

When $R_2$ and/or $R_8$ are alkyl groups, these especially signify methyl or alkyl branched in the $\alpha$ position, e.g. the tert.butyl group.

When A is an alkylene chain, this preferably contains 2 to 3 carbon atoms and especially signifies the propylene group.

A especially signifies the $=N-COOR_7$ group or the $=N-CO-(CH_2)_m-R_6$ group; $R_7$ preferably signifies ethyl, and $R_6$ preferably signifies phenyl or o-fluorophenyl.

When $R_5$ is alkyl or alkenyl, the alkyl groups preferably contain 2 to 4 carbon atoms; the alkenyl groups preferably contain 3 carbon atoms.

When a phenyl group in the substituent $R_5$ is substituted by alkyl, alkoxy or alkylmercapto, these groups especially contain 1 or 2, preferably one carbon atom.

When $R_7$ is alkyl or alkenyl, the alkyl group especially contains two carbon atoms, and the alkenyl group especially contains 3 carbon atoms. When $R_7$ is phenylalkyl, this especially contains 7 to 9 carbon atoms. When $R_7$ is phenylalkenyl, this especially contains 8 or 9 carbon atoms.

X preferably signifies chlorine or bromine, especially chlorine.

The reaction of the invention in accordance with process variant (a) may be carried out in conventional manner for such nucleophilic substitution reactions. For example, the reaction may be effected by reacting a compound of formula IIa with an excess of hydrazine, e.g. 5 to 10 mols of hydrazine calculated on 1 mol of a compound of formula II. Alternatively there may be present another basic agent capable of binding any acid which may result during the reaction, e.g. a tertiary amine or an alkali metal or alkaline earth metal hydroxide or carbonate. The reaction may, for example, be effected in the presence of an inert, preferably polar organic solvent, e.g. a lower mono-, di- or tri-hydroxy alcohol such as glycerin, ethanol or isopropanol, dimethylformamide or an open chain or cyclic ether such as dioxane, diethylene glycol dimethyl ether or tetrahydrofuran. An excess of hydrazine may alternatively be used as solvent. When a compound of formula IIa,

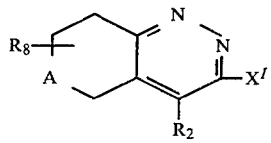

IIa wherein $X^I$ is chlorine, bromine or mercapto, and
$R_2$, $R_8$ and A are as defined above, is used, the reaction may, for example, be effected in hydrazine hydrate. Suitable reaction temperatures are between about 20° and about 150° C., preferably a temperature between 80° and 120° C. or the boiling temperature of the reaction mixture.

When a compound of formula IIb,

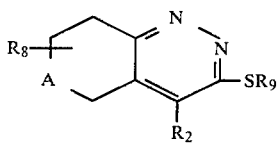

IIb wherein $R_2$, $R_8$, $R_9$ and A are as defined above, is used, the reaction may alternatively be effected in an autoclave at a temperature between 80° and 150° C.

Process variant (b) may be effected under the reaction conditions known for the preparation of analogous hydrazones. For example, there may be present an inert, preferably polar organic solvent, e.g. a lower alcohol such as methanol, ethanol or isopropanol, or an open chain or cyclic ether, e.g. diethylene glycol dimethyl ether, tetrahydrofuran or dioxane, or acetone. The reaction temperature may be from 0° C. to the boiling temperature. The product may be isolated by evaporating the reaction mixture to dryness or allowing the crude product to crystallize out of the reaction mixture or after concentrating the reaction mixture.

The resulting compounds of formula I may be isolated from the reaction mixture and purified in accordance with known methods. Acid addition salt forms may be obtained from the free base forms in known manner and vice versa.

The compounds of formula II, required as starting materials, are new and may, for example, be obtained as follows:

A compound of formula IIb may, for example, be obtained by reacting a compound of formula IIc,

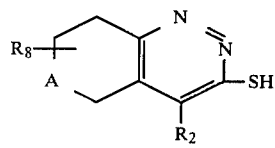

IIc wherein $R_2$, $R_8$ and A are as defined above, with a compound of formula IV, $$R_9 X^{II}$$  IV wherein $R_9$ is as defined above, and
$X^{II}$ is chlorine or bromine, in a polar organic solvent and in the presence of an acid-binding agent.

A compound of formula IIc may, for example, be obtained by reacting a compound of formula IId,

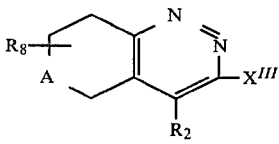

IId wherein $R_2$, $R_8$ and A are as defined above, and
$X^{III}$ is chlorine or bromine, with thiourea or optionally with sodium sulphide.

A compound of formula IIe,

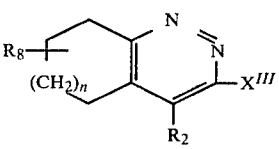

IIe wherein $R_2$, $R_8$, $X^{III}$ and n are as defined above, may, for example, be obtained by heating a compound of formula Va,

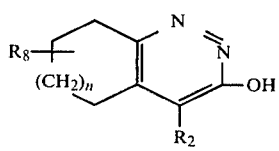

Va wherein $R_2$, $R_8$ and n are as defined above, with a suitable chlorinating or brominating agent, e.g. phosphorus oxychloride, phosphorus trichloride or pentachloride or phosphorus oxybromide.

A compound of formula IIf,

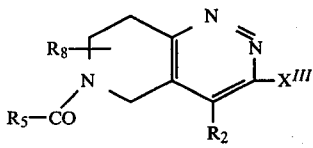
IIf wherein $R_2$, $R_5$, $R_8$ and $X^{III}$ are as defined above, may, for example, be obtained by reacting a compound of formula VI,

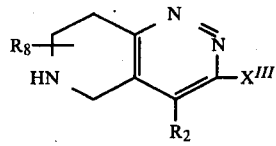
VI wherein $R_2$, $R_8$ and $X^{III}$ are as defined above, with a compound of formula VII,

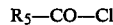
VII wherein $R_5$ is as defined above,
in an inert solvent in the presence of an acid-binding agent. A compound of formula VI may be obtained by heating a compound of formula VIII,

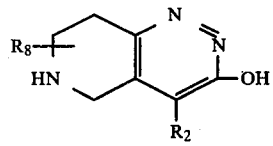
VIII wherein $R_2$ and $R_8$ are as defined above, with a suitable chlorinating or brominating agent, e.g. phosphorus oxychloride, phosphorus trichloride or pentachloride or phosphorus oxybromide. A compound of formula VIII may be obtained by removing the —$COOR_7^I$ group with an acid from a compound of formula Vb,

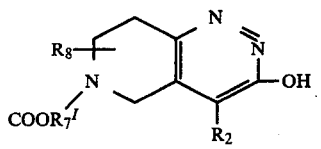
Vb wherein
$R_2$ and $R_8$ are as defined above, and
$R_7^I$ is lower alkyl.

A compound of formula V,

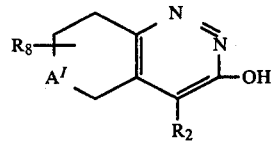
V wherein
$R_2$ and $R_8$ are as defined above, and
$A^I$ is a —$(CH_2)_n$— group,
wherein n is as defined above, or an =N—$COOR_7^I$ group, wherein $R_7^I$ is as defined above, may, for example, be obtained by cyclizing a compound of formula IX,

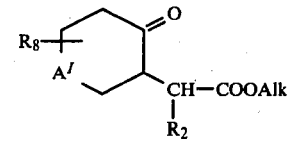
IX wherein $A^I$, $R_2$ and $R_8$ are as defined above, and Alk is lower alkyl,
in an inert solvent, in the presence of at least an equivalent amount of glacial acetic acid with hydrazine hydrate or a salt of hydrazine, and oxidizing the resulting compound of formula X,

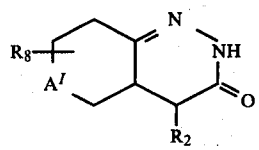
X wherein $R_2$, $R_8$ and $A^I$ are as defined above, preferably with bromine.

A compound of formula IX may, for example, be obtained by reacting a compound of formula XI,

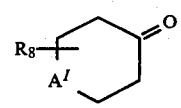
XI wherein $R_8$ and $A^I$ are as defined above, with a secondary, preferably a cyclic amine such as, e.g., pyrrolidine, morpholine or piperidine, to obtain an enamine of formula XII,

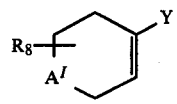
XII wherein
$R_8$ and $A^I$ are as defined above, and
Y is a secondary amino group,
adding a compound of formula XIII,

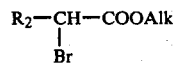
XIII wherein $R_2$ and Alk are as defined above, to the enamine obtained above, heating the reaction mixture and removing the enamine group from the resulting reaction product of formula XIV,

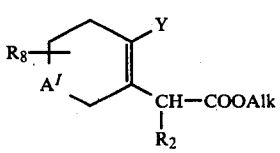
XIV wherein $A^I$, $R_2$, $R_8$, Alk and Y are as defined above, by heating with water.

Insofar as the production of the starting materials is not described, these are known or may be produced in accordance with known processes, or in a manner analogous to the processes described herein or to known processes.

In the following non-limitative Examples all temperatures are indicated in degrees Centigrade.

EXAMPLE 1:

3-hydrazino-5,6,7,8-tetrahydro-4,8-dimethyl-6-pyrido[4,3-c]pyridazine-carboxylic acid ethyl ester [process variant (a)]

22.7 g of 3-chloro-5,6,7,8-tetrahydro-4,8-dimethyl-6-pyrido[4,3-c]pyridazine-carboxylic acid ethyl ester are suspended in 180 cc of hydrazine hydrate and the suspension is stirred at a bath temperature of 100° for 6½ hours. After cooling the reaction mixture with ice, the crude title compound is filtered off and recrystallized from 65 cc of absolute ethanol. M.P. 173°–175° (decomp.).

The starting material may be produced as follows:

(a) A mixture of 92.2 g of 1-carbethoxy-3-methyl-4-piperidone and 53.5 g of pyrrolidine in 1.0 liter of benzene is heated to the boil at reflux for 2 hours and the resulting water is continuously removed azeotropically. The reaction mixture is concentrated and the crude 1,2,3,6-tetrahydro-3-methyl-4-pyrrolidinylpyridine-1-carboxylic acid ethyl ester, obtained as an oil, is used as such for the next reaction.

(b) A mixture of 242.3 g of 1,2,3,6-tetrahydro-3-methyl-4-pyrrolidinylpyridine-1-carboxylic acid ethyl ester and 271.5 g of 2-bromo-propionic acid ethyl ester in 750 cc of acetonitrile is heated at reflux for 20 hours while stirring. A solution of 30 g of sodium acetate in 400 cc of water is added to the reaction mixture and this is again heated to the boil at reflux for 2 hours. The mixture is completely concentrated and the oily residue is divided between 700 cc of benzene and 400 cc of water. The organic phase is separated, dried over sodium sulphate and concentrated. The resulting crude 1-carbethoxy-3-methyl-4-piperidone-5-(2-propionic acid ethyl ester) is purified by vacuum distillation, B.P. 150°–160° at 0.3 mm of Hg.

(c) 109.7 g of 1-carbethoxy-3-methyl-4-piperidone-5-(2-propionic acid ethyl ester) and 19.3 g of hydrazine hydrate are stirred at reflux for 4 hours in 500 cc of absolute ethanol and 40 cc of glacial acetic acid. The reaction solution is completely concentrated in a vacuum and the residue is divided between 400 cc of chloroform and 200 cc of a 10% aqueous caustic soda solution. The organic phase is separated, washed with 100 cc of wate, dried over sodium sulphate, filtered and concentrated to a yellow-orange oil. Further purification is effected by chromatography of the crude product on an aluminium oxide column. The fractions eluted with chloroform/1% of methanol may be crystallized with ether and yield the analytically pure 2,3,4,4a,5,6,7,8-octahydro-4,8-dimethyl-3-oxo-6-pyrido[4,3-c]pyridazine-carboxylic acid ethyl ester having a M.P. of 102°–104° (decomp.).

(d) A mixture of 19.6 g of bromine in 50 cc of chloroform is added dropwise within 50 minutes to a boiling solution of 31.0 g of 2,3,4,4a,5,6,7,8-octahydro-4,8-dimethyl-3-oxo-6-pyrido[4,3-c]-pyridazine-carboxylic acid ethyl ester in 150 cc of chloroform and the mixture is stirred at the same temperature for a further hour. After cooling, 150 cc of ice water are added, the organic phase is separated, washed with 50 cc of water, dried over sodium sulphate, filtered and the filtrate is concentrated to a crystalline residue. After recrystallizing once from 100 cc of absolute ethanol, 6-carbethoxy-5,6,7,8-tetrahydro-4,8-dimethyl-3(2H)-pyrido[4,3-c]pyridazinone, having a M.P. of 166°–168° (decomp.), is obtained.

(e) 40.6 g of 6-carbethoxy-5,6,7,8-tetrahydro-4,8-dimethyl-3(2H)-pyrido[4,3-c]pyridazinone are suspended in 200 cc of phosphorus oxychloride and the suspension is heated to the boil while stirring. Upon heating a complete solution results, which is stirred at the boil for a total of one hour and is then concentrated to an oil in a vacuum. 500 cc of ice/water and 200 cc of a concentrated aqueous caustic soda solution are added and the reaction product is extracted with a total of 500 cc of chloroform. The chloroform phase is dried over sodium sulphate, filtered and concentrated and the resulting oily crude product is crystallized with ether, whereby 3-chloro-5,6,7,8-tetrahydro-4,8-dimethyl-6-pyrido[4,3-c]pyridazine-carboxylic acid ethyl ester, having a M.P. of 73°–74°, is obtained.

EXAMPLE 2:

3-hydrazino-5,6,7,8-tetrahydro-4-methyl-6-pyrido[4,3-c]pyridazine-carboxylic acid ethyl ester The title compound is produced in a manner analogous to that described in Example 1, using 3-chloro-5,6,7,8-tetrahydro-4-methyl-6-pyrido[4,3-c]pyridazine-carboxylic acid ethyl ester as starting material. The crystalline crude product is purified by producing the fumarate, having a M.P. of 130°–132°. This is converted into the crystalline title compound, having a M.P. of 175°–177° (decomp.), with 10% aqueous ammonia.

The starting material may be produced in a manner analogous to that described in Example 1, steps (b) to (e); the following compounds are obtained using 1,2,3,6-tetrahydro-4-pyrrolidinylpyridine-1-carboxylic acid ethyl ester as starting material:

(a) 1-carbethoxy-4-piperidone-3-(2-propionic acid ethyl ester) (B.P. 170°–180° at 0.3 mm of Hg).

(b) 2,3,4,4a,5,6,7,8-octahydro-4-methyl-3-oxo-6-pyrido[4,3-c]pyridazine-carboxylic acid ethyl ester [M.P. 134°–136° (decomp.) from carbon tetrachloride].

(c) 6-carbethoxy-5,6,7,8-tetrahydro-4-methyl-3(2H)pyrido[4,3-c]pyridazinone [M.P. 175°–178° (decomp.) from ethanol].

(d) 3-chloro-5,6,7,8-tetrahydro-4-methyl-6-pyrido[4,3-c]-pyridazine-carboxylic acid ethyl ester (M.P. 70°–71° from ether/hexane).

EXAMPLE 3:

6-(o-fluorobenzoyl)-3-hydrazino-5,6,7,8-tetrahydro-4-methylpyrido[4,3-c]pyridazine The title compound is produced in a manner analogous to that described in Example 1, using 3-chloro-6-(o-fluorobenzoyl)-5,6,7,8-tetrahydro-4-methyl-pyrido[4,3-c]pyridazine as starting material. M.P. of the title compound 193° to 196° (decomp.) from ethanol/methanol 3:1.

The starting material may be produced as follows:

A suspension of 14.4 g of 6-carbethoxy-5,6,7,8-tetrahydro-4-methyl-3(2H)pyrido[4,3-c]pyridazinone in 100 cc of concentrated hydrochloric acid is heated to the boil at reflux for 20 hours while stirring. The resulting 5,6,7,8-tetrahydro-4-methyl-3(2H)pyrido[4,3-c]pyridazinone is isolated (M.P. of the hydrochloride 344° to 348°) and is converted in a manner analogous to that described in Example 1(e) into 3-chloro-5,6,7,8-tetrahydro-4-methylpyrido[4,3-c]pyridazine (M.P. of the maleate: 170° to 173°), this is reacted with o-fluorobenzoyl chloride, whereby 3-chloro-6-(o-fluorobenzoyl)-5,6,7,8-tetrahydro-4-methylpyrido[4,3-c]pyridazine is obtained (M.P. 151°–153°).

EXAMPLE 4:
6-benzoyl-3-hydrazino-5,6,7,8-tetrahydro-4-methyl-pyrido[4,3-c]pyridazine The title compound is produced in a manner analogous to that described in Example 1, using 6-benzoyl-3-chloro-5,6,7,8-tetrahydro-4-methylpyrido[4,3-c]pyridazine as starting material. [M.P. of the title compound 153°–155° (decomp.) from ethanol].

The crude product is purified by producing the crystalline fumarate, M.P. 149°–152°.

The 6-benzoyl-3-chloro-5,6,7,8-tetrahydro-4-methyl-pyrido[4,3-c]pyridazine [M.P. 145°–147° (decomp.) from ethanol], required as starting material, may be produced in a manner analogous to that described in Example 3, using benzoyl chloride in place of o-fluorobenzoyl chloride.

EXAMPLE 5:
6-benzoyl-3-hydrazino-5,6,7,8-tetrahydro-4,8-dimethyl-pyrido[4,3-c]pyridazine The title compound is produced in a manner analogous to that described in Example 1, using 6-benzoyl-3-chloro-5,6,7,8-tetrahydro-4,8-dimethylpyrido[4,3-c]pyridazine as starting material [M.P. of the title compound 215°–218° (decomp.) from ethanol/methanol 2:1].

The starting material may be produced in a manner analogous to that described in Example 3, using 6-carbethoxy-5,6,7,8-tetrahydro-4,8-dimethyl-3(2H)pyrido[4,3-c]pyridazinone as starting material. The following intermediates are isolated:
(a) 5,6,7,8-tetrahydro-4,8-dimethyl-3(2H)pyrido[4,3-c]pyridazinone hydrochloride [M.P. 330° to 334° (decomp.) from methanol/water].
(b) 3-chloro-5,6,7,8-tetrahydro-4,8-dimethylpyrido[4,3-c]pyridazine [M.P. of the maleate 152°–154° (decomp.) from methanol].
(c) 6-benzoyl-3-chloro-5,6,7,8-tetrahydro-4,8-dimethylpyrido[4,3-c]pyridazine (oil).

EXAMPLE 6:
3-hydrazino-5,6,7,8-tetrahydro-4-phenyl-6-pyrido[4,3-c]pyridazine-carboxylic acid ethyl ester The title compound is produced in a manner analogous to that described in Example 1, using 3-chloro-5,6,7,8-tetrahydro-4-phenyl-6-pyrido[4,3-c]pyridazine-carboxylic acid ethyl ester as starting material. [M.P. of the title compound 176°–179° (decomp.) from ethanol].

The starting material is obtained in a manner analogous to that described in Example (1b) to (e), using 1,2,3,6-tetrahydro-4-pyrrolidinylpyridine-1-carboxylic acid ethyl ester as starting material. The following intermediates are isolated:
(a) 1-carbethoxy-4-piperidone-3-(2-phenyl-acetic acid ethyl ester) (B.P. 205°–210° at 0.3 mm of Hg).
(b) 2,3,4,4a,5,6,7,8-octahydro-3-oxo-4-phenyl-6-pyrido[4,3-c]pyridazine-carboxylic acid ethyl ester [M.P. 217°–220° (decomp.) from ethanol].
(c) 6-carbethoxy-5,6,7,8-tetrahydro-4-phenyl-3(2H)pyrido[4,3-c]pyridazinone [M.P. 230°–233° (decomp.) from ethanol].
(d) 3-chloro-5,6,7,8-tetrahydro-4-phenyl-6-pyrido[4,3-c]pyridazine-carboxylic acid ethyl ester [M.P. 105°–107° (decomp.) from ether].

EXAMPLE 7:
3-hydrazino-6,7,8,9-tetrahydro(5H)-4-methyl-cyclohepta[c]pyridazine The title compound is produced in a manner analogous to that described in Example 1, using 3-chloro-6,7,8,9-tetrahydro(5H)-4-methyl-cyclohepta[c]pyridazine as starting material. [M.P. 198°–200° (decomp.) from absolute ethanol].

The starting material may be produced in a manner analogous to that described in Example 1, steps (c) to (e); the following compounds are obtained using cycloheptanone-2-(2-propionic acid ethyl ester) as starting material:
(a) 2,3,4,4a,5,6,7,8,9-octahydro(5H)-4-methylcyclohepta[c]pyridazinone(3) (M.P. 74°–76° from ether/hexane).
(b) 6,7,8,9-tetrahydro(5H)-3-hydroxy-4-methylcyclohepta[c]pyridazine (M.P. 214°–215° from ether).
(c) 3-chloro-6,7,8,9-tetrahydro(5H)-4-methylcyclohepta[c]pyridazine (M.P. 83°–84° from ethyl acetate).

EXAMPLE 8:
3-hydrazino-5,6,7,8,9,10-hexahydro-4-methyl-cycloocta[c]pyridazine The title compound is produced in a manner analogous to that described in Example 1, using 3-chloro-5,6,7,8,9,10-hexahydro-4-methyl-cycloocta[c]pyridazine as starting material. [M.P. of the title compound 214°–216° (decomp.) from absolute ethanol; M.P. of the fumarate of the title compound: 161°–163° (decomp.) from absolute ethanol].

The starting material may be produced in a manner analogous to that described in Example 1, steps (a) to (e); the following compounds are obtained using cyclooctanone as starting material:
(a) 1-pyrrolidinyl-cyclooctene (1) (oil-crude)
(b) 1-pyrrolidinyl-cyclooctene (1)-2-(2-propionic acid ethyl ester) (oil-crude)
(c) 4,4a,5,6,7,8,9,10-octahydro-4-methyl-cycloocta[c]pyridazin-3(2H)-one [M.P. 133°–135° (decomp.) from ethanol/ether 1:1]
(d) 5,6,7,8,9,10-hexahydro-4-methyl-cycloocta[c]pyridazin-3-ol [M.P. 226°–229° (decomp.) from absolute ethanol]
(e) 3-chloro-5,6,7,8,9,10-hexahydro-4-methyl-cycloocta[c]-pyridazine [M.P. 88°–89° (decomp.) from ethyl acetate].

EXAMPLE 9:
3-isopropylidene-hydrazino-5,6,7,8-tetrahydro-4-methyl-6-pyrido[4,3-c]pyridazinecarboxylic acid ethyl ester [process variant (b)]

3.8 g of crystallized 3-hydrazino-5,6,7,8-tetrahydro-4-methyl-6-pyrido[4,3-c]pyridazine-carboxylic acid ethyl ester are suspended in 60 cc of acetone and the solution which gradually results is heated on a water bath for 10 minutes. The solution is subsequently concentrated and the resulting title compound is recrystallized from ether/isopropanol. M.P. of the title compound: 105–107 (decomp.).

The following compounds are obtained in a manner analogous to that described in Example 9:

6-(o-fluorobenzoyl)-5,6,7,8-tetrahydro-3-isopropylidene-hydrazino-4-methylpyrido[4,3-c]pyridazine

[M.P. 191°–193° (decomp.) from ethanol]
using 6-(o-fluorobenzoyl)-3-hydrazino-5,6,7,8-tetrahydro-4-methylpyrido[4,3-c]pyridazine as starting material;

5,6,7,8-tetrahydro-3-isopropylidene-hydrazino-4,8-dimethyl-6-pyrido[4,3-c]-pyridazine-carboxylic acid ethyl ester

[M.P. 125°–126° (decomp.) from ethanol]
using 3-hydrazino-5,6,7,8-tetrahydro-4,8-dimethyl-6-pyrido[4,3-c]pyridazine-carboxylic acid ethyl ester as starting material;

5,6,7,8-tetrahydro-3-isopropylidene-hydrazino-4-methyl-cinnoline

[M.P. 169°–170° (decomp.) from ethanol]
using 3-hydrazino-5,6,7,8-tetrahydro-4-methylcinnoline as starting material;

6,7,8,9-tetrahydro(5H)-3-isopropylidene-hydrazino-4-methyl-cyclohepta[c]pyridazine

[M.P. 153°–154° (decomp.) from absolute ethanol]
using 3-hydrazino-6,7,8,9-tetrahydro(5H)-4-methylcyclohepta[c]pyridazine as starting material;

5,6,7,8,9,10-hexahydro-3-isopropylidene-hydrazino-4-methyl-cycloocta[c]pyridazine

[M.P. of the fumarate 181°–182° (decomp.) from absolute ethanol]
using 3-hydrazino-5,6,7,8,9,10-hexahydro-4-methylcycloocta[c]pyridazine as starting material.

EXAMPLE 10

Using process variant (a) as described in Example 1 there is made the compound of formula Ia wherein A is =N.CO.OEt, R₂ is n-butyl and R₈ is hydrogen, which is converted using process variant (b) as described in Example 9 into the corresponding compound of formula Ib wherein R₃ and R₄ are both methyl.

In analogous manner to that described in Example 1, there are obtained the following compounds of formula Ia, where A is =N—CO—R₅ and R₂ is methyl and R₈ is hydrogen,

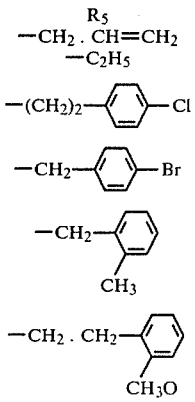

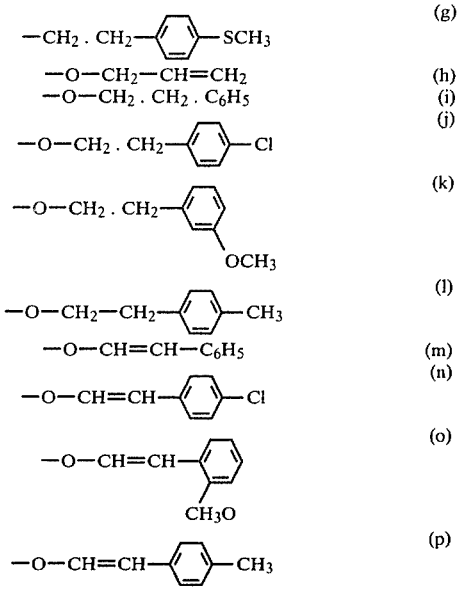

The compounds of formula I are useful as anti-hypertensive agents, as indicated by standard tests, e.g. in hypertonic Grollman rats in accordance with the method of A. Grollman [Proc. Soc. Exper. Biol. Med., 57, 102 (1944)] on s.c. administration of from 0.03 to 3 mg/kg animal body weight of the compounds.

For this use the dosage will, of course, vary depending on the compound employed, mode of administration and treatment desired. However, in general, satisfactory results are obtained when administered at a daily dosage of from about 0.03 mg to about 3 mg per kg animal body weight, conveniently given in divided doses 2 to 4 times a day or in sustained release form. For the larger mammals, the total daily dosage is in the range from about 2 to about 200 mg, and dosage forms suitable for oral administration comprise from about 0.5 to about 100 mg of the compounds admixed with a solid or liquid pharmaceutical carrier or diluent.

The compounds of formula I may be administered in pharmaceutically acceptable acid addition salt form. Such acid addition salt forms exhibit the same order of activity as the free base forms and are readily prepared in conventional manner. Representative acid addition salt forms include organic acid salt forms such as the hydrogen maleate, fumarate, tartrate and methane sulphonate and mineral acid salt forms such as the hydrochloride, hydrobromide and sulphate. A pharmaceutical composition may comprise a compound of formula I, in free base form or in pharmaceutically acceptable acid addition salt form, in association with a pharmaceutical carrier or diluent. Such compositions conveniently contain more than 1% by weight of the compound of formula I and may be prepared by conventional techniques to be in conventional forms, for example, capsules, tablets, suppositories, dispersible powders, syrups, elixirs, suspensions or solutions, for enteral or parenteral administration. Suitable pharmaceutical diluents or carriers include, for example, water, alcohols, natural or hardened oils and waxes, calcium and sodium carbonates, calcium phosphate, kaolin, talc and lactose as well as suitable preserving agents, such as ethyl-p-hydroxybenzoate, suspending agents such as methyl cellulose, tragacanth and sodium alginate, wetting agents such as lecithin, polyoxyethylene stearate and polyoxyethylene sorbitan mono-oleate, granulating and disintegrating agents such as starch and alginic acid, binding agents such as starch, gelatin and acacia, and lubricating agents such as magnesium stearate, stearic acid and talc, in order to provide an elegant and palatable pharmaceutical preparation. Compositions in tablet form may be coated by conventional techniques to delay disintegration of the tablet and absorption of the active ingredient in the gastrointestinal tract and thereby provide sustained action over a long period.

The preferred compositions from the standpoint of ease of administration are solid compositions, particularly solid-filled gelatin capsules and tablets.

Especially interesting are compounds of formula Ic,

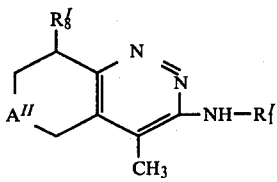

Ic wherein $R_1^I$ is amino or $-N=C(CH_3)_2$,
$R_8^I$ is hydrogen or methyl, and
$A^{II}$ is $=N-COR_5^I$,
  wherein $R_5^I$ is ethoxy, phenyl, or phenyl monosubstituted in the o position by fluorine,
  or $-(CH_2)_3-$.

The preferred compounds of formula Ic are 3-hydrazino-5,6,7,8-tetrahydro-4,8-dimethyl-6-pyrido[4,3-c]pyridazinecarboxylic acid ethyl ester, 6-benzoyl-3-hydrazino-5,6,7,8-tetrahydro-4,8-dimethyl-pyrido[4,3-c]pyridazine, 3-hydrazino-5,6,7,8-tetrahydro-4-methyl-6-pyrido[4,3-c]-pyridazinecarboxylic acid ethyl ester and 3-hydrazino-5,6,7,8,9,10-hexahydro-4-methylcycloocta[c]pyridazine.

I claim:

1. A compound of formula I,

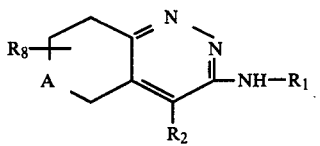

I wherein
$R_1$ is amino, or

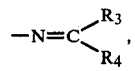

wherein each of $R_3$ and $R_4$ is independently alkyl of 1 to 4 carbon atoms,
$R_2$ phenyl,
$R_8$ is hydrogen or alkyl of 1 to 4 carbon atoms, and
$A$, $=N-CO-R_5$,
  wherein $R_5$ is alkyl of 1 to 6 carbon atoms, alkenyl of 3 to 6 carbon atoms, a $-(CH_2)_m-R_6$ group,
    wherein m is an integer from 0 to 2, and
    $R_6$ is phenyl, or phenyl monosubstituted by fluorine, chlorine, bromine, alkyl of 1 to 4 carbon atoms, alkoxy of 1 to 4 carbon atoms or alkylmercapto of 1 to 4 carbon atoms,
  or an $-OR_7$ group,
    wherein $R_7$ is alkyl of 1 to 4 carbon atoms, alkenyl of 2 to 4 carbon atoms, phenylalkyl of 7 to 10 carbon atoms, phenylalkyl of 7 to 10 carbon atoms monosubstituted in the phenyl ring by chlorine, alkoxy of 1 to 4 carbon atoms or alkyl of 1 to 4 carbon atoms; phenylalkenyl of 8 to 10 carbon atoms, or phenylalkenyl of 8 to 10 carbon atoms monosubstituted in the phenyl ring by chlorine, alkoxy of 1 to 4 carbon atoms or alkyl of 1 to 4 carbon atoms,
or a pharmaceutically acceptable acid addition salt thereof.

2. The compound of claim 1, which is 3-hydrazino-5,6,7,8-tetrahydro-4-phenyl-6-pyrido[4,3-c]pyridazinecarboxylic acid ethyl ester.

3. A compound of claim 1, wherein $R_1$ is amino.

4. A compound of claim 1, wherein $R_1$ is

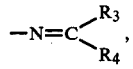

5. A pharmaceutical composition for use in the treatment of hypertension consisting essentially of an antihypertensive effective amount of a compound of claim 1, in association with a pharmaceutical carrier or diluent.

6. A method of treating hypertension in animals consisting essentially of administering to an animal in need of such treatment an antihypertensive effective amount of a composition of claim 5.

* * * * *